United States Patent [19]

Mogensen et al.

[11] Patent Number: 5,886,153
[45] Date of Patent: Mar. 23, 1999

[54] ANTIBODIES DIRECTED AGAINST THE ALPHA INTERFERON RECEPTOR

[75] Inventors: Knud Erik Mogensen; Gilles Uze; Georges Lutfalla; Ion Gresser, all of Paris, France

[73] Assignee: Societe LEB-TECH, Paris, France

[21] Appl. No.: 471,453

[22] Filed: Jun. 6, 1995

(Under 37 CFR 1.47)

Related U.S. Application Data

[62] Division of Ser. No. 453,090, May 30, 1995, which is a continuation of Ser. No. 900,642, filed as PCT/FR90/00758, Oct. 19, 1990, abandoned.

[30] Foreign Application Priority Data

Oct. 20, 1989 [FR] France .................................. 89/13770

[51] Int. Cl.$^6$ ..................................... C07K 16/28
[52] U.S. Cl. .................. 530/387.9; 530/351; 530/387.1; 436/512; 435/69.1
[58] Field of Search ................................ 530/387.1, 350, 530/387.9, 351; 435/69.1; 436/512

[56] References Cited

U.S. PATENT DOCUMENTS 5,516,515  5/1996  Vellucci ................................ 424/184.1

OTHER PUBLICATIONS

Uze et al, *Cell* 60:225–234 (1990).
Eid et al, *J. Interferon Res.* 7(6):762 (1987).
Shearer et al, *J. Cell. Biochem. Supple.* (12 Part A):216 (1988).
Mouchel–Vielh et al, *FEBS* 313(3):255–259 (1992).
Lutfalla et al, *J. Biol. Chem.* 267(4):2802–09 (1992).
Langer et al, *Somatic Cell & Molecular Genetics* 16(3):231–240 (1990).
Langer et al, *BBRC* 157(3):1264–1270 (1988).
Colamonici et al, *Proc. Natl. Acad. Sci USA* 87(18):7230–34 (1990).
Meadows et al, *J. Interferon Res.* 10(Suppl. 1):5159 (1990).
Branca, *J. Interferon Res.* 7(1):77–85 (1987).
Meadows et al, *Proc. Am. Assoc. Cancer Res.* 31:55 (1990).
Traub et al, *J. Biol. Chem.* 259(22):13872–77 (1984).
Siemens, *Pro. Am. Assoc. Cancer Res.* 31:238 (1990).
Gaboriaud et al, *FEBS* 269(1):1–3 (1990).
Eid et al, *Biochem. Biophys. Acta* 1034(1):114–117 (1990).
Shulman et al, *J. Interferon Res.* 8(1) (1988) "Molecular cloning of the human IFN–alpha, beta receptor cDNA", p. S16, abstract No. 3–9.
Revel et al, *ICSU Short Reports*, vol. 4, 1986 "Interferon receptor and interferon–activated genes", pp. 362–365.
Epstein et al, *Biochemical and Biophysical Research Communications*, 107(3):1060–1066 (Aug. 16, 1982), Academic Press, Inc., (New York, US) "Direct evidence that the gene product of the human chromosome 21 locus, IFRC, is the interferon–alpha receptor".
Raziuddin et al, *Proceedings National Academy Science*, vol. 81, Sep. 1984, "Receptors for human alpha and beta interferon but not for gamma interferon are specified by human chromosome 21", pp. 5504–5508.
Dunbar et al., Methods in Enzymology, 182, 663, 1990.
Faltynek et al., Proc. Acad. Sci., 80, 3269, Jun. 1983.
Uze et al., Proc. Natl. Acad. Sci, 89, 4774–4778, May 1992.

*Primary Examiner*—Sally P. Teng
*Attorney, Agent, or Firm*—Nixon & Vanderhye P.C.

[57] ABSTRACT

The present invention relates to antibodies against an alpha interferon receptor, as well as to kits comprising such antibodies. The antibodies of the invention are suitable for the assay of the receptors or for their visualization in the case of imaging. The present antibodies and kits can thus be used as diagnostics or imaging agents, or as pharmacological models to test compounds derived from human alpha interferon.

5 Claims, 9 Drawing Sheets

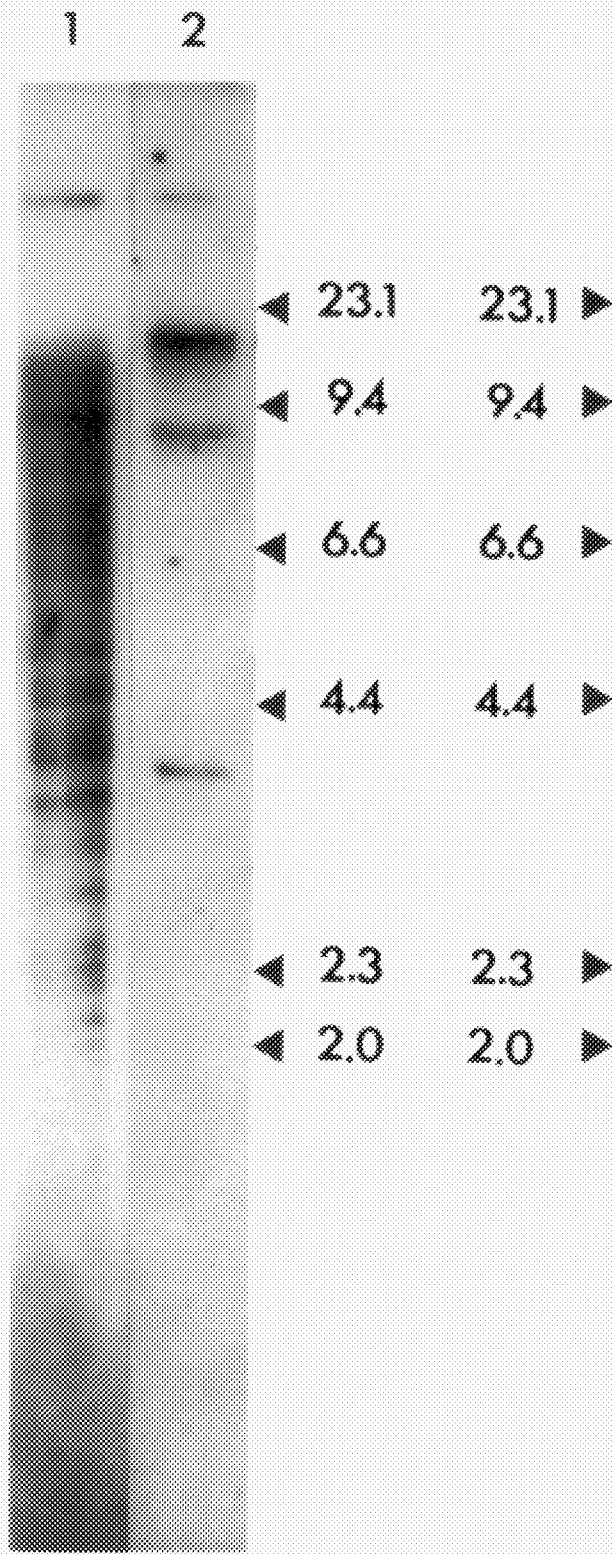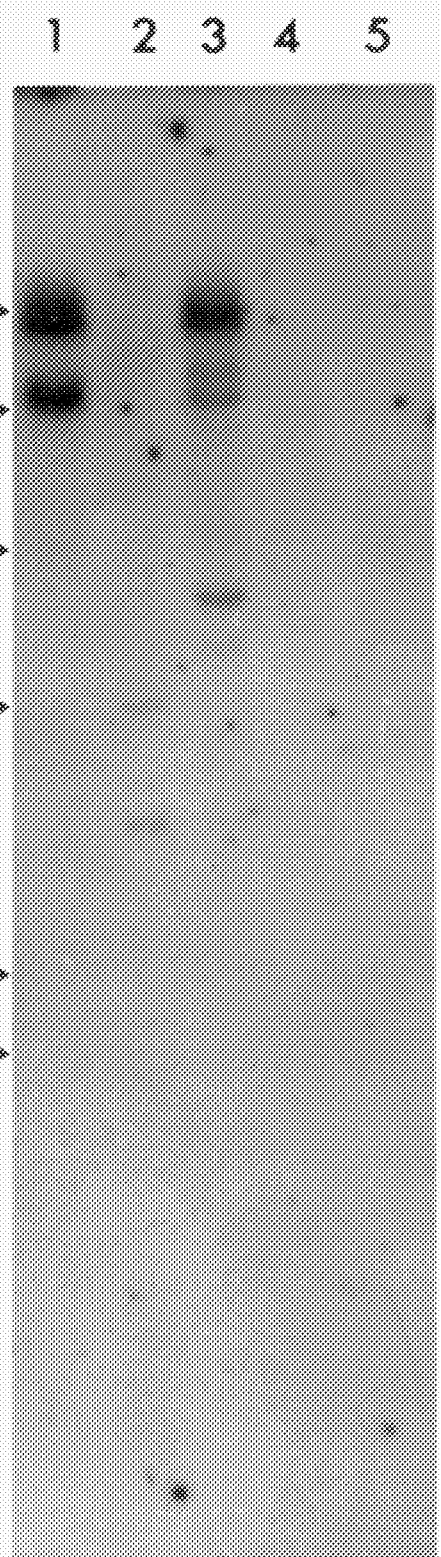

```
TTAGGACGGGGCGATGGGCGGCTGAGAGGAGCTGCGCGTGCGCGAACATGTAACTGGTGG

GATCTGCGGCGGGCTCCCAG ATG ATG GTC GTC CTC CTG GGC GCG ACG ACC         108
                     Met Met Val Val Leu Leu Gly Ala Thr Thr          10

CTA GTG CTC GTC GCC GTG GGC CCA TGG GTG TTG TCC GCA GCC GCA
Leu Val Leu Val Ala Val Gly Pro Trp Val Leu Ser Ala Ala Ala

GGT GGA AAA AAT CTA AAA TCT CCT CAA AAA GTA GAG GTC GAC ATC         198
Gly Gly Lys Asn Leu Lys Ser Pro Gln Lys Val Glu Val Asp Ile          40

ATA GAT GAC AAC TTT ATC CTG AGG TGG AAC AGG AGC GAT GAG TCT
Ile Asp Asp Asn Phe Ile Leu Arg Trp Asn Arg Ser Asp Glu Ser

GTC GGG AAT GTG ACT TTT TCA TTC GAT TAT CAA AAA ACT GGG ATG         288
Val Gly Asn Val Thr Phe Ser Phe Asp Tyr Gln Lys Thr Gly Met          70

GAT AAT TGG ATA AAA TTG TCT GGG TGT CAG AAT ATT ACT AGT ACC
Asp Asn Trp Ile Lys Leu Ser Gly Cys Gln Asn Ile Thr Ser Thr

AAA TGC AAC TTT TCT TCA CTC AAG CTG AAT GTT TAT GAA GAA ATT         378
Lys Cys Asn Phe Ser Ser Leu Lys Leu Asn Val Tyr Glu Glu Ile         100
```

Fig. 4A

```
AAA TTG CGT ATA AGA GCA GAA AAA GAA AAC ACT TCT TCA TGG TAT    468
Lys Leu Arg Ile Arg Ala Glu Lys Glu Asn Thr Ser Ser Trp Tyr    130

GAG GTT GAC TCA TTT ACA CCA TTT CGC AAA GCT CAG ATT GGT CCT    558
Glu Val Asp Ser Phe Thr Pro Phe Arg Lys Ala Gln Ile Gly Pro    160

CCA GAA GTA CAT TTA GAA GCT GAA GAT AAG GCA ATA GTG ATA CAC
Pro Glu Val His Leu Glu Ala Glu Asp Lys Ala Ile Val Ile His

ATC TCT CCT GGA ACA AAA GAT AGT GTT ATG TGG GCT TTG GAT GGT
Ile Ser Pro Gly Thr Lys Asp Ser Val Met Trp Ala Leu Asp Gly

TTA AGC TTT ACA TAT AGC TTA CTT ATC TGG AAA AAC TCT TCA GGT    648
Leu Ser Phe Thr Tyr Ser Leu Leu Ile Trp Lys Asn Ser Ser Gly    190

GTA GAA GAA AGG ATT GAA AAT ATT TAT TCC AGA CAT AAA ATT TAT
Val Glu Glu Arg Ile Glu Asn Ile Tyr Ser Arg His Lys Ile Tyr

AAA CTC TCA CCA GAG ACT ACT TAT TGT CTA AAA GTT AAA GCA GCA
Lys Leu Ser Pro Glu Thr Thr Tyr Cys Leu Lys Val Lys Ala Ala

CTA CTT ACG TCA TGG AAA ATT GGT GTC TAT AGT CCA GTA CAT TGT    738
Leu Leu Thr Ser Trp Lys Ile Gly Val Tyr Ser Pro Val His Cys    220
```

*Fig. 4B*

```
ATA AAG ACC ACA GTT GAA AAT GAA CTA CCT CCA GAA AAT ATA
Ile Lys Thr Thr Val Glu Asn Glu Leu Pro Pro Glu Asn Ile

GAA GTC AGT GTC CAA AAT CAG AAC TAT GTT CTT AAA TGG GAT TAT    828
Glu Val Ser Val Gln Asn Gln Asn Tyr Val Leu Lys Trp Asp Tyr   250

ACA TAT GCA AAC ATG ACC TTT CAA GTT CAG TGG CTC CAC GCC TTT
Thr Tyr Ala Asn Met Thr Phe Gln Val Gln Trp Leu His Ala Phe

TTA AAA AGG AAT CCT GGA AAC CAT TTG TAT AAA TGG AAA CAA ATA    918
Leu Lys Arg Asn Pro Gly Asn His Leu Tyr Lys Trp Lys Gln Ile   280

CCT GAC TGT GAA AAT GTC AAA ACT ACC CAG TGT GTC TTT CCT CAA
Pro Asp Cys Glu Asn Val Lys Thr Thr Gln Cys Val Phe Pro Gln

AAC GTT TTC CAA AAA GGA ATT TAC CTT CTC CGC GTA CAA GCA TCT   1008
Asn Val Phe Gln Lys Gly Ile Tyr Leu Leu Arg Val Gln Ala Ser   310

GAT GGA AAT AAC ACA TCT TTT TGG TCT GAA GAG ATA AAG TTT GAT
Asp Gly Asn Asn Thr Ser Phe Trp Ser Glu Glu Ile Lys Phe Asp

ACT GAA ATA CAA GCT TTC CTA CTT CCT CCA GTC TTT AAC ATT AGA   1098
Thr Glu Ile Gln Ala Phe Leu Leu Pro Pro Val Phe Asn Ile Arg   340
```

Fig. 4C

```
TCC CTT AGT GAT TCA TTC CAT ATC TAT ATC GGT GCT CCA AAA CAG   1188
Ser Leu Ser Asp Ser Phe His Ile Tyr Ile Gly Ala Pro Lys Gln    370

TCT GGA AAC ACG CCT GTG ATC CAG GAT TAT CCA CTG ATT TAT GAA   1188
Ser Gly Asn Thr Pro Val Ile Gln Asp Tyr Pro Leu Ile Tyr Glu    370

ATT ATT TTT TGG GAA AAC ACT TCA AAT GCT GAG AGA AAA ATT ATC
Ile Ile Phe Trp Glu Asn Thr Ser Asn Ala Glu Arg Lys Ile Ile

GAG AAA AAA ACT GAT GTT CCT AAT TTG AAA CCA CTG ACT            1278
Glu Lys Lys Thr Asp Val Pro Asn Leu Lys Pro Leu Thr            400

GTA TAT TGT GTG AAA GCC AGA GCA CAC ACC ATG GAT GAA AAG CTG
Val Tyr Cys Val Lys Ala Arg Ala His Thr Met Asp Glu Lys Leu

AAT AAA AGC AGT GTT TTT AGT GAC GCT GTA TGT GAG AAA ACA AAA   1368
Asn Lys Ser Ser Val Phe Ser Asp Ala Val Cys Glu Lys Thr Lys   430

CCA GGA AAT ACC TCT AAA ATT TGG CTT ATA GTT GGA ATT TGT ATT
Pro Gly Asn Thr Ser Lys Ile Trp Leu Ile Val Gly Ile Cys Ile

GCA TTA TTT GCT CTC CCG TTT GTC ATT TAT GCT GCG AAA GTC TTC   1458
Ala Leu Phe Ala Leu Pro Phe Val Ile Tyr Ala Ala Lys Val Phe   460
```

```
TTG AGA TGC ATC AAT TAT GTC TTC TTT CCA TCA CTT AAA CCT TCT
Leu Arg Cys Ile Asn Tyr Val Phe Phe Pro Ser Leu Lys Pro Ser

TCC AGT ATA GAT GAG TAT TTC TCT GAA CAG CCA TTG AAG AAT CTT   1548
Ser Ser Ile Asp Glu Tyr Phe Ser Glu Gln Pro Leu Lys Asn Leu    490

CTG CTT TCA ACT TCT GAG GAA CAA ATC GAA AAA TGT TTC ATA ATT
Leu Leu Ser Thr Ser Glu Glu Gln Ile Glu Lys Cys Phe Ile Ile

GAA AAT ATA AGC ACA ATT GCT ACA GTA GAA GAA ACT AAT CAA ACT   1638
Glu Asn Ile Ser Thr Ile Ala Thr Val Glu Glu Thr Asn Gln Thr    520

GAT GAA GAT CAT AAA AAA TAC AGT TCC CAA ACT AGC CAA GAT TCA
Asp Glu Asp His Lys Lys Tyr Ser Ser Gln Thr Ser Gln Asp Ser

GGA AAT TAT TCT AAT GAA GAT GAA AGC GAA AGT AAA ACA AGT GAA   1728
Gly Asn Tyr Ser Asn Glu Asp Glu Ser Glu Ser Lys Thr Ser Glu    550

GAA CTA CAG CAG GAC TTT GTA TGACCAGAAATGAACTGTGTCAAGTATAAGG
Glu Leu Gln Gln Asp Phe Val

TTTTCAGCAGGAGTTACACTGGGAGCCTGAGGTCCTCACCTTCCTCTCAGTAACTACAG   1840
                                                              557
```

```
AGAGGACGTTTCCTGTTTAGGGAAAGAAAAACATCTTCAGATCATAGGTCCTAAAAAT

ACGGGCAAGCTCTTAACTATTTAAAATGAAATTACAGGCCCGGGCACGGTGGCTCACACC  1960

TGTAATCCCAGCACTTTGGGAGGCTGAGGCAGGCAGATCATGAGGTCAAGAGATCGAGA

CCAGCCTGGCCAACGTGGTGAAACCCCATCTCTACTAAAATACAAAAATTAGCCGGGTAG  2080

TAGGTAGGCGCGCGCCTGTGTCTTAGCTACTCAGGAGGCTGAGGCAGGAGAATCGCTT

GAAAACAGGAGGTGGAGGTTGCAGTGAGCCGAGATCACGCCACTGCACTCCAGCCTGGTGA  2200

CAGCGTGAGACTCTTAAAAAGAAATTAAAAGAGTTGAGACAAACGTTTCCTACATT

CTTTTCCATGTGTAAAATCATGAAAAAGCCTGTCACCGGACTTGCATTGGATGAGATGAGT  2320

CAGACCAAAACAGTGGCCACCCGTCTTCCCTGTGAGCCTAAGTGCAGCCGTGCTAGC

TGCGCACCGTGGCTAAGGATGACGTCTGTGTTCCTGTCCATCACTGATGCTGCTGGCTACT  2440

GCATGTGCCACACCTGTGTCGTTCGCCATTCCTAACATTCTGTTTCATTCTTCCTCGGGA

GATATTTCAAACATTGGTCTTTTTCTTTTAACACTGAGGGTAGGCCCTTAGGAAATTATT  2560

TAGGAAAGTCTGAACACGTTATCACTGGTTTTCTGGAAAGTAGCTTACCCTAGAAAAC

AGCTGCAAATGCCAGAAAGATGATCCCTAAAAATGTTGAGGGACTTCTGTTCATTCATCCC  2680

GAGAACATTGGCTTCCACATCACAGTATCTACCCTTACATGGTTTAGGATTAAAGCCAG

GCAATCTTTTACTATGAAAAAAAAAAAAAAAAAAAAA                          2784
```

Fig. 4F

ANTIBODIES DIRECTED AGAINST THE ALPHA INTERFERON RECEPTOR

This is a division of Application No. 08/453,090, filed May 30, 1995, which is a continuation of Application No. 07/900,642, filed Jun. 15, 1992, now abandoned, which claims priority from PCT/FR90/00758, filed Oct. 19, 1990.

The present invention relates to the sequence, in particular to a cDNA sequence, coding for the gene for the alpha interferon receptor.

Interferon is a generic term specifying three antigenic classes: alpha, beta and gamma, of proteins capable of inducing, among other things, an antiviral state and of inhibiting the multiplication of sensitive cells.

Between the alpha and beta interferons, which are produced as a consequence of viral infection, there exists a sufficiently extensive structural homology for these two types of interferon to be able to react via the same cell receptor.

Human alpha interferon is itself a mixture of a dozen proteins with very extensive homology, encoded by different structural genes. These subtypes have an identical functional spectrum but their specific activities are different.

Gamma interferon, which is produced by activated lymphocytes, does not possess any homology with the alpha/beta interferons and it does not react with their receptor.

At present, the structures of the interferons (which possess about 165 amino acids) are quite well known as regards their amino acid sequences and several studies have been directed towards the analysis of the functional domains of these proteins. Hybrid molecules, constructed between the interferons of high and low affinity by using restriction sites on the DNA coding for these interferons, have been used to show that the N-terminal part of the molecule determines the affinity of binding to its cell receptor and, consequently, the specific activity of the alpha interferons.

Respiratory diseases of viral origin pose considerable economic problems for public health. Clinical trials have shown that alpha interferon provides 100% protection to volunteers infected with different rhinoviruses. Similarly, it has been demonstrated that among volunteers treated with alpha interferon and infected with a coronavirus, 6% develop the symptoms of a cold compared with 37% of the volunteers treated with placebo.

Nonetheless, although human alpha interferon was found to be efficacious in these trials, the toxicity that it exerts on the nasal mucosa poses a major problem.

Interferon also possesses an antitumoral activity in man and at present it has become the treatment of choice for some cancers. However, interferon injected by the systemic route also exerts toxicity on the nervous system which limits the possibilities of treatment.

In fact, at present, there is no means of determining which interferon should be used to obtain therapeutic activity and reduced toxicity. Several laboratories have made considerable efforts to construct modified interferons which might have pronounced activity associated with low toxicity. This approach has been shown to be disappointing.

It is now obvious that the possible success of such a project requires knowledge of the structure of the receptor of the interferons in order to devise the structure of an agonist. An agonist having a high activity and low toxicity for the nasal mucosa would find a very large market for the treatment of respiratory diseases of viral origin.

That is why the present invention relates more particularly to the production of a protein having the structure of the alpha interferon receptor and its expression, in particular at the surface of cells, as well as the DNA sequences coding for the said protein.

Hence, the present invention relates, in the first instance, to the human alpha interferon receptor characterized in that it corresponds to the sequence shown in FIG. 4 or to one of its allelic variants which does not differ from it by more than 3 amino acids.

These allelic variants may include the sequence shown in FIG. 4 in which the threonine at position 164 is replaced by an arginine and an aspartic acid is inserted between the aspartic acid at position 479 and the glutamic acid at position 480.

The present invention also relates to a DNA sequence coding for the receptor for human alpha interferon.

This DNA sequence will preferably correspond to the sequence shown in FIG. 4 or to a sequence allelic with the latter.

The structure of the DNA sequence coding for the receptor for human alpha interferon is analysed in the examples. In particular, it bears a signal peptide. In some cases, it will be possible to delete or replace this signal peptide by another signal peptide but in most cases it will be preferable to retain this signal peptide shown in FIG. 4 and hence the corresponding coding sequence.

This sequence is preferably inserted into a system which ensures its cellular expression in a suitable host cell, in particular at a transmembrane site.

In particular, the present invention relates to the DNA fragment, in particular the cDNA fragment, characterized in that it codes for the gene of the alpha interferon receptor. In particular, it will correspond to the sequence shown in FIG. 4 or to a sequence allelic with the latter.

It may thus be the DNA sequence shown in FIG. 4 in which the cytosine at position 569 is replaced by guanine and a TGA codon inserted between the adenine situated at position 1514 and the thymine at position 1515.

The present invention also relates to non-human cells characterized in that they express the said receptor for human alpha interferon and to a process for the production of the said cells.

According to this process, compatible host cells are transfected or infected with an element of DNA bearing a DNA sequence coding for the said receptor, as well as the elements capable of ensuring the expression of this sequence in the said cell.

The examples given hereafter demonstrate how it has been possible to express this sequence coding for the receptor for human alpha interferon (IFN-alpha h) in non-human mammalian cells, in particular mouse cells. The procedures which make possible the cell expression of exogenous DNA sequences are known. Depending on the host cells, it may be a question of using self-replicating vectors such as plasmids or integrating vectors, DNA sequences or viral vectors for example. In the case in which it is desired to produce a cell line expressing the human IFN-alpha receptor, the procedure used may be a low yield procedure since only one line is sought. On the other hand, when the production of the protein alone is desired, it is preferable to use vectors ensuring amplification, in particular plasmid vectors comprising an origin of replication or multicopy systems of integration.

In addition, the present invention relates to a process for the preparation of human alpha IFN receptors.

Thus, when it is desired to produce the protein alone, host cells transformed, transfected or infected by an expression vector for the said protein, comprising a DNA sequence coding for the said receptor under the control of a promoter of transcription of this sequence in the host as well as the elements ensuring the translation of the protein, will be cultivated in a suitable culture medium and then the protein obtained will be separated by any appropriate means.

This protein will be used to prepare antibodies, in particular monoclonal antibodies directed against the receptor; the appropriate technology will not be described in detail since it is a known procedure.

The invention thus makes it possible to produce:
the receptor for human alpha interferon,
antibodies directed against this receptor, and
cells expressing the said receptor.

The applications of these elements are very varied. First, the receptor in isolation or expressed on the surface of a cell may enable analogues of human alpha interferon to be tested in order to define the best agonists.

This type of test may also be performed by means of the corresponding protein attached to a solid support such as plates, beads, etc. . . These procedures have already been used for other receptors or for antigen-antibody assays.

The receptor agonist assays may be performed by measuring direct binding or by measuring displacements which make it possible to estimate the affinity of the agonist in relation to a reference substance, for example the human alpha IFN.

The antibodies will be used for the assay of the receptors or for their visualization in the case of imaging. These are procedures which make it possible to evaluate certain pathological conditions justifying, for example, treatment with alpha interferon or which make it possible to evaluate certain conditions in which the level of these receptors varies.

Hence, the invention also relates to diagnostic kits containing one or more of the preceding elements as a diagnostic or imaging agent, or as a pharmacological model to test the compounds derived from human alpha interferon.

The receptor protein or the corresponding antibodies may also be used as a pharmacological agent when it is desired to block the human alpha IFN receptors or when the protein is used as an inhibitor to block human alpha IFN in certain states in which the over-expression of human alpha interferon may be harmful.

Finally, the antibodies may be used as targetting agent for the insertion of an active principle coupled to this antibody in the vicinity of a receptor for the human alpha IFN.

The examples and figures given hereafter are non-limiting and will make it possible to demonstrate other advantages and characteristics of the present invention.

BRIEF DESCRIPTION OF THE DRAWINGS

FIGS. 2A and 2B represent the "Southern blot" analysis of the genomic DNA of the primary and secondary transfectants.
FIG. 2A
Well No. 1: EcoRI digestion of the DNA of the primary clone 10BH7 hybridized with a Alu probe.
Well No. 2: same DNA hybridized with a Lambda probe.
FIG. 2B
Wells No. 1 and 3: BamHI digestion of the DNA of the two secondary transfectants 1B4D10 and 2A415 hybridized with a Alu probe.
Well No. 2 and 4: BamHI digestion of the DNA of two negative secondary transfectants hybridized with a Alu probe.
Well No. 5: BamHI digestion of the DNA of the parental cells BTG 9A hybridized with a Alu probe.

FIGS. 4A–4F show the nucleotide sequence of the cDNA of the receptor for human alpha interferon (SEQ ID NO:1) as well as its amino acid sequence (SEQ ID NO:2). The signal peptide and the transmembrane region are shown in boxes. The glycosylation sites linked to nitrogen are underlined by dashes. The two polyadenylation sites and the Sma I restriction site are underlined.

EXAMPLE 1

Figure 1B:
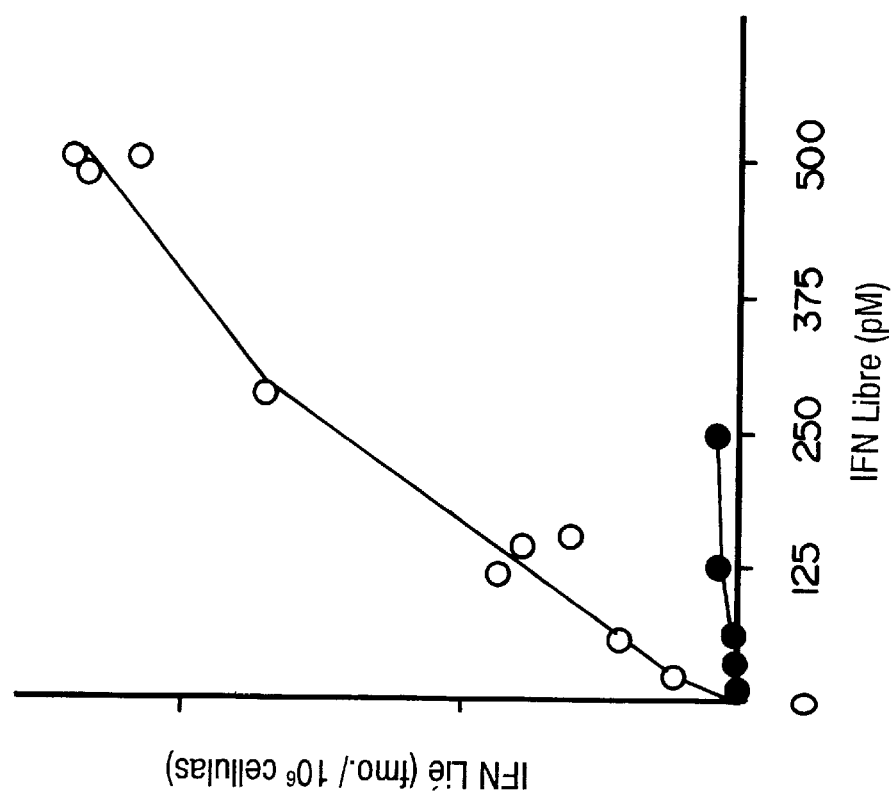
FIGS. 1A and 1B show the binding curves of human alpha interferon B (black symbols) or the hybrid BDBB (white symbols) to the primary transfectant 10BH7 (FIG. 1A) or to the parental cells BTG 9A (FIG. 1B).

Selection of transfected BTG mouse cells sensitive to human alpha B interferon

Mouse BTG 9A cells are co-transfected with a human cDNA bank cloned in a mammalian lambda phage expression vector also containing the bacterial gene neo and the genomic DNA Daudi of high molecular weight in a ratio 1:1. This system of co-transfection in which the expression of a human interferon receptor may result from the genomic human DNA and/or the human cDNA is used to increase the chances of isolating useful transfectants.

Clones of stable transfectants are selected in a G418 medium at a frequency of $10^{-2}$–$10^{-2}$. In order to detect cell clones sensitive to human alpha interferon, transfected clones are treated with 30,000 units/ml of human B interferon and infected with VSV. At this concentration, mouse BTG cells are insensitive to alpha B interferon but a transfectant clone expressing the receptor gene for human alpha interferon ought to be in an antiviral phase.

In view of the fact that the interferon titer is inversely proportional to the multiplicity of infection, this viral selection makes it possible to neutralize the large quantity of VSV produced by the majority of the clones of the unsuitable cells which would abolish the antiviral state of the clone of the cell of interest. This method implies a rapid absorption of the virus by the cells followed by a treatment with rabbit anti-VSV antiserum to neutralize the excess of the virus, and development of the cytopathic effect in a rabbit anti-VSV antiserum containing a semi-solid gelose medium. Surviving cellular clones are isolated individually. In order to avoid a chronic VSV infection, the cell clones are subjected to a treatment with mouse alpha/beta interferon and the anti-VSV antiserum is maintained in a G-418 medium for one week. They are then retested for their sensitivity to human alpha B interferon in relation to the VSV or EKC infections. Most of these transfected clones are insensitive to human alpha B interferon. Nonetheless, one clone showed an interesting sensitivity to human alpha B interferon. It was then subcloned and designated 10B H7.

The sensitivity of the 10B H7 cells to numerous mouse and human alpha interferons was determined, then the behaviour of these cells was compared with that of the parental mouse BTG cells.

Table I shows the activity of mouse alpha/beta interferon, human alpha B interferon, human beta interferon and human gamma interferon tested on mouse parental BTG cells of the transfected 10B H7 clone and of human Wish cells using both the VSV and the EMC viruses.

With respect to mouse interferon, the 10B H7 cells are as sensitive as the parental BTG cells. Moreover, the 10B H7 cells show a sensitivity at least 64,000 times greater to human alpha B interferon than the parental cells. The activity of human beta interferon on the 10B H7 cells is also observed to be increased 8-fold but no antiviral activity of human gamma interferon is detected since it is recognized by a different receptor on both the parental BTG cells and on the transfected 10B H7 clone. The specific antiviral activity of alpha B interferon ($4.7 \times 10^6$ units/mg) on the 10B H7 cells is of the order of the specific activities of the human alpha interferons on human cells.

TABLE I

| | Antiviral activities of interferon preparations tested on: (units/ml) | | | |
|---|---|---|---|---|
| | BTG | 10BH7 | WISH | RATIO 10BH7/BTG |
| Mouse alpha/beta IFN | $12.8 \times 10^6$ | $12,3 \times 10^6$ | 240 | 1 |
| Human alpha B IFN | <20 | $1,27 \times 10^6$ | $5.4 \times 10^6$ | >64,000 |
| Human beta IFN | 200 | $1,6 \times 10^3$ | $2,7 \times 10^6$ | 8 |
| Human gamma IFN | $<1 \times 10^3$ | $<1 \times 10^3$ | $20 \times 10^6$ | — |

EXAMPLE 2

Transfectants of a mouse BTG cell sensitive to interferon which express the receptor for human interferon.

Human alpha B interferon behaves towards 10B H7 cells like alpha D interferon on human cells, with similar specific activity and similar apparent binding affinity. Like alpha D interferon on human cells, the binding of human alpha B interferon to 10B H7 cells may be measured only at 37° C.

Several binding experiments were performed with iodinated alpha B interferon used as probe for the human receptor and a iodinated hybrid interferon designated BDBB which is active on both the parental mouse lines and on the clone 10B H7, as positive control. This hybrid interferon which has a specific activity on mouse cells close to that of human alpha B interferon on the 10B H7 cells, could be a probe for the mouse and human receptors on both the parental BTG cells and the transfected 10B H7 cells.

Figure 1A:
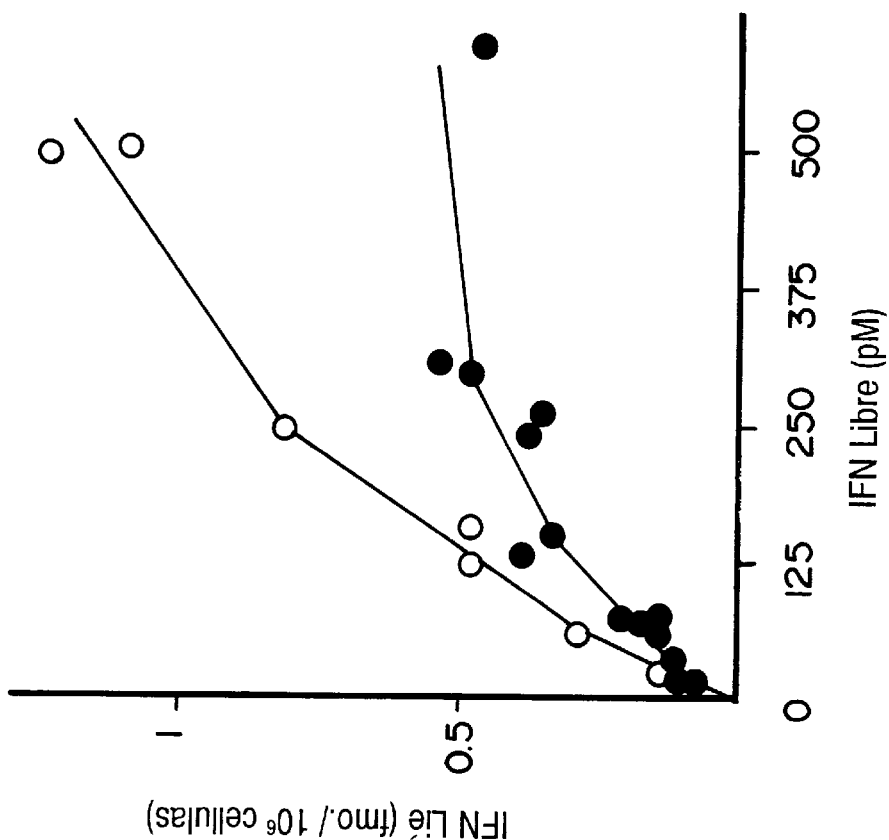

FIGS. 1A and 1B show that the binding of BDBB is similar to the BTG and 10B H7 cells. Conversely, the 10B H7 cells bind alpha B interferon specifically whereas the BTG cells do not. The binding parameters calculated from the Scatchard data show that the 10B H7 cells express about 500 binding sites per cell for alpha B interferon with an apparent Kd of $2.10^{-10}$M. This is similar to the values for the BDBB interferon (1,500 binding sites per cell; apparent KD $5.10^{-10}$M), which is active on both the parental mouse lines and on the clone 10B H7.

In conclusion these results, supplemented with other studies, indicate that human alpha B interferon binds to a specific receptor on the 10B H7 cells but not to the parental mouse cells.

EXAMPLE 3

Cloning of a probe covering the gene for the human alpha interferon receptor in clones of a secondary transfected cell Starting from the hypothesis that the 10B H7 cells express a transfected human gene necessary for conferring binding sites and an antiviral activity of alpha B interferon on a mouse cell, the distribution of the human DNA in the transfected 10B H7 genome was investigated.

FIG. 2A is a "Southern blot" with the DNA of the 10B H7 clone using either a human Alu sequence which detects human genomic DNA or a probe with lambda DNA in order to detect the integrated cDNA.

Thus it was shown that the transfectants had integrated more than one part per 1000 of human Daudi DNA and 100 copies of the human cDNA of the mammalian library. In view of the considerable amount of human DNA in this clone, it was necessary to isolate secondary transfectants in order to clone the DNA sequence responsible for the expression of the receptor in the initial 10B H7 clone. For this purpose, mouse BTG cells were co-transfected with genomic DNA from the 10B H7 clone and from neopSV2. Cells sensitive to human interferon were isolated. The stable secondary transfectants were subjected to 4 cycles of treatment with alpha B interferon and to VSV infection. After subcloning, two independent secondary clones 1B4D10 and 2A415 were obtained. These two secondary clones are independent but are derived from the same initial clone. They have the same characteristics as those of the initial clone 10B H7, i.e. sensitivity to human alpha interferon and expression of the receptor at their surface. These two secondary clones have not retained the sequences associated with the lambda phages in their genome and, consequently, the expression of the receptors for human alpha interferon is due to the genomic DNA of the Daudi cells which had been transfected initially into the BTG cells. They have, in fact, conserved the human genomic sequences. FIG. 2B shows a BamHI digestion of the secondary DNA clones hybridized with a Alu probe which detects the repetitive Alu sequences. The two positive secondary clones 1B4D10 and 2A415 have in common a main band of 18 kb.

A Alu probe was used to screen fragments of size 20–15 kb of a genomic library after complete digestion of the DNA of the secondary clone 1B4D10 by BamHI cloned in a lambda phage EMBL 3. The repeated Alu sequences containing the BamHI fragment of 18 kb were isolated and then subcloned in a plasmid vector pUC.

This fragment contains two EcoRI sites giving end fragments of 11 kb and 2 kb and a central fragment of 5 kb. There are human Alu repetitive sequences in these three fragments and thus the central 5 kb fragment must be deleted from the DNA sequences of the mouse. The central 5 kb EcoRI fragment is present in a EcoRI digestion of the DNA of the two secondary clones 1B4D10 and 2A415, obtained independently from the same initial clone.

EXAMPLE 4

Figure 3:
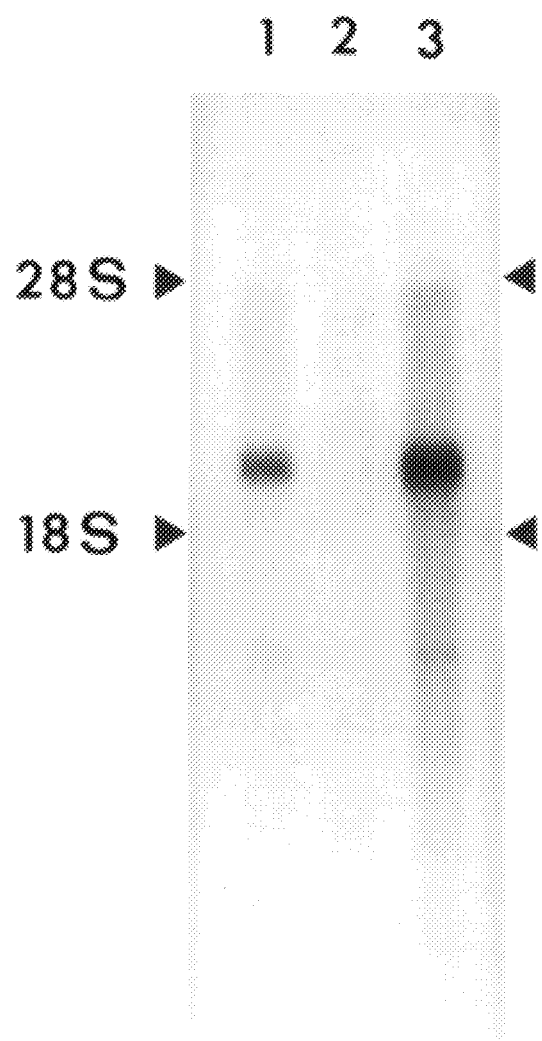
FIG. 3 shows the "Northern blot" analysis of the RNA polyA$^+$ of the two secondary transfectants (wells No. 1 and 3) and of the parental cells (well No. 2) hybridized with the probe EcoRI 5 kb.

Cloning and nucleotide sequence of the cDNA of the receptor for human alpha interferon FIG. 3 shows that the 5 kb EcoRI probe detects a transcript of equal size in the secondary clones which is absent from the RNA poly A⁺ of the parental BTG cells.

A cDNA library prepared in a lambda ZapII phage vector from the RNA of the secondary clone 1B4D10 is screened and the cDNA hybridizing with the 5 kb EcoRI probe is isolated. Eight independent cDNA clones, all bearing the same 3' end, are analysed by sequencing. The longest (1900 bp) have at their 5' end a HindIII restriction fragment of 400 bp covering only the coding sequences and lack the repetitive elements. Used as a probe, this fragment detects the 2.5 kb transcript present in both the secondary clones and in the Daudi human cells but which is absent from the mouse BTG. In view of the fact that point mutations may arise in transfected genes, this HindIII probe of 400 bp has been used to study a lambda ZapII cDNA library starting from Daudi human cells in order to isolate complete cDNA clones corresponding to the human transcript.

Overlapping cDNAs isolated from human Daudi cDNA libraries were preserved in "pBluescript" plasmids starting from the in vivo excision of ZapII lambda by f1 helper phages. The single-stranded DNA recovered in the presence of the M13 intermediate phage from bacteria containing "pBluescript" plasmids is sequenced at one end of the cDNA by the chain termination method (Sanger et al. 1977) and the sequences of the other end of the cDNA are obtained from the sequence of the double strand in the plasmid. Oligo-nucleotides were synthesized and used in particular for sequencing the DNA when "gaps" appeared in the sequence.

The two strands of the longest cDNAs described in FIGS. 4A–4F were completely sequenced.

The sequence of cDNA is of the order of 2784 bp and contains an untranslated region of 1035 bp at the 3' end which includes two polyadenylation sequences ATTAAA. The sequence of the open reading frame is complete since it is terminated at the 5' end by a STOP codon. Two ATG codons are found side by side at positions 79 and 82.

In addition to the hydrophobic region of the amino terminus, a second hydrophobic region (amino acids 456 to 476) was identified. There are 15 potential glycosylation sites linked to nitrogen, 12 in the putative extracellular domain and 3 in the putative intracellular domain.

The molecular weight of the sequence suggested as receptor (including the signal peptide) is 63,485 Dalton, and glycosylation may give rise to a value of the order of 95,000–100,000 Dalton for the protein of the naturally occurring receptor.

The receptor for human alpha interferon appears to be a single protein. Its sequence nonetheless exhibits a certain allelic variation. Such variation is found, for example, in the Daudi heterozygbte cells which express two alleles of the receptor, the one corresponding to the sequence described in FIGS. 4A–4F, the other exhibiting a substitution of a cytosine by a guanine at position 569 and the insertion of three bases T, G and A after the adenine situated at position 1514. At the level of the protein, this results in a substitution of the threonine 164 by an arginine, and by the insertion of an aspartic acid after the aspartic acid 479.

We claim:

1. An isolated antibody, wherein said antibody binds specifically to a human alpha interferon receptor that comprises the sequence of SEQ ID NO:2.

2. A kit comprising:
(1) at least one antibody according to claim 1, and
(2) reagents for an antigen-antibody assay.

3. The kit according to claim 2, wherein said kit further comprises a solid support.

4. The kit according to claim 3, wherein said solid support is a plate or a bead.

5. An isolated antibody that recognizes a human alpha interferon receptor, wherein said antibody has been raised with an immunogen comprising an isolated recombinant human alpha interferon receptor comprising the sequence from residues 28–557 of SEQ ID NO:2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2784 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TTAGGACGGG  GCGATGGCGG  CTGAGAGGAG  CTGCGCGTGC  GCGAACATGT  AACTGGTGGG      60

ATCTGCGGCG  GCTCCCAGAT  GATGGTCGTC  CTCCTGGGCG  CGACGACCCT  AGTGCTCGTC     120

GCCGTGGGCC  CATGGGTGTT  GTCCGCAGCC  GCAGGTGGAA  AAAATCTAAA  ATCTCCTCAA     180

AAAGTAGAGG  TCGACATCAT  AGATGACAAC  TTTATCCTGA  GGTGGAACAG  GAGCGATGAG     240

TCTGTCGGGA  ATGTGACTTT  TTCATTCGAT  TATCAAAAAA  CTGGGATGGA  TAATTGGATA     300

AAATTGTCTG  GGTGTCAGAA  TATTACTAGT  ACCAAATGCA  ACTTTTCTTC  ACTCAAGCTG     360

AATGTTTATG  AAGAAATTAA  ATTGCGTATA  AGAGCAGAAA  AAGAAAACAC  TTCTTCATGG     420

TATGAGGTTG  ACTCATTTAC  ACCATTTCGC  AAAGCTCAGA  TTGGTCCTCC  AGAAGTACAT     480

TTAGAAGCTG  AAGATAAGGC  AATAGTGATA  CACATCTCTC  CTGGAACAAA  AGATAGTGTT     540

ATGTGGGCTT  TGGATGGTTT  AAGCTTTACA  TATAGCTTAC  TTATCTGGAA  AAACTCTTCA     600

GGTGTAGAAG  AAAGGATTGA  AAATATTTAT  TCCAGACATA  AAATTTATAA  ACTCTCACCA     660

GAGACTACTT  ATTGTCTAAA  AGTTAAAGCA  GCACTACTTA  CGTCATGGAA  AATTGGTGTC     720

TATAGTCCAG  TACATTGTAT  AAAGACCACA  GTTGAAAATG  AACTACCTCC  ACCAGAAAAT     780

ATAGAAGTCA  GTGTCCAAAA  TCAGAACTAT  GTTCTTAAAT  GGGATTATAC  ATATGCAAAC     840

ATGACCTTTC  AAGTTCAGTG  GCTCCACGCC  TTTTTAAAAA  GGAATCCTGG  AAACCATTTG     900

TATAAATGGA  AACAAATACC  TGACTGTGAA  AATGTCAAAA  CTACCCAGTG  TGTCTTTCCT     960

CAAAACGTTT  TCCAAAAAGG  AATTTACCTT  CTCCGCGTAC  AAGCATCTGA  TGGAAATAAC    1020
```

| | | | | | |
|---|---|---|---|---|---|
| ACATCTTTTT | GGTCTGAAGA | GATAAAGTTT | GATACTGAAA | TACAAGCTTT | CCTACTTCCT | 1080 |
| CCAGTCTTTA | ACATTAGATC | CCTTAGTGAT | TCATTCCATA | TCTATATCGG | TGCTCCAAAA | 1140 |
| CAGTCTGGAA | ACACGCCTGT | GATCCAGGAT | TATCCACTGA | TTTATGAAAT | TATTTTTTGG | 1200 |
| GAAAACACTT | CAAATGCTGA | GAGAAAAATT | ATCGAGAAAA | AAACTGATGT | TACAGTTCCT | 1260 |
| AATTTGAAAC | CACTGACTGT | ATATTGTGTG | AAAGCCAGAG | CACACACCAT | GGATGAAAAG | 1320 |
| CTGAATAAAA | GCAGTGTTTT | TAGTGACGCT | GTATGTGAGA | AAACAAAACC | AGGAAATACC | 1380 |
| TCTAAAATTT | GGCTTATAGT | TGGAATTTGT | ATTGCATTAT | TTGCTCTCCC | GTTTGTCATT | 1440 |
| TATGCTGCGA | AAGTCTTCTT | GAGATGCATC | AATTATGTCT | TCTTTCCATC | ACTTAAACCT | 1500 |
| TCTTCCAGTA | TAGATGAGTA | TTTCTCTGAA | CAGCCATTGA | AGAATCTTCT | GCTTTCAACT | 1560 |
| TCTGAGGAAC | AAATCGAAAA | ATGTTTCATA | ATTGAAAATA | TAAGCACAAT | TGCTACAGTA | 1620 |
| GAAGAAACTA | ATCAAACTGA | TGAAGATCAT | AAAAAATACA | GTTCCCAAAC | TAGCCAAGAT | 1680 |
| TCAGGAAATT | ATTCTAATGA | AGATGAAAGC | GAAAGTAAAA | CAAGTGAAGA | ACTACAGCAG | 1740 |
| GACTTTGTAT | GACCAGAAAT | GAACTGTGTC | AAGTATAAGG | TTTTTCAGCA | GGAGTTACAC | 1800 |
| TGGGAGCCTG | AGGTCCTCAC | CTTCCTCTCA | GTAACTACAG | AGAGGACGTT | TCCTGTTTAG | 1860 |
| GGAAAGAAAA | AACATCTTCA | GATCATAGGT | CCTAAAAATA | CGGGCAAGCT | CTTAACTATT | 1920 |
| TAAAAATGAA | ATTACAGGCC | CGGGCACGGT | GGCTCACACC | TGTAATCCCA | GCACTTTGGG | 1980 |
| AGGCTGAGGC | AGGCAGATCA | TGAGGTCAAG | AGATCGAGAC | CAGCCTGGCC | AACGTGGTGA | 2040 |
| AACCCCATCT | CTACTAAAAA | TACAAAAATT | AGCCGGGTAG | TAGGTAGGCG | CGCGCCTGTT | 2100 |
| GTCTTAGCTA | CTCAGGAGGC | TGAGGCAGGA | GAATCGCTTG | AAAACAGGAG | GTGGAGGTTG | 2160 |
| CAGTGAGCCG | AGATCACGCC | ACTGCACTCC | AGCCTGGTGA | CAGCGTGAGA | CTCTTTAAAA | 2220 |
| AAGAAATTA | AAAGAGTTGA | GACAAACGTT | TCCTACATTC | TTTTCCATGT | GTAAAATCAT | 2280 |
| GAAAAAGCCT | GTCACCGGAC | TTGCATTGGA | TGAGATGAGT | CAGACCAAAA | CAGTGGCCAC | 2340 |
| CCGTCTTCCT | CCTGTGAGCC | TAAGTGCAGC | CGTGCTAGCT | GCGCACCGTG | GCTAAGGATG | 2400 |
| ACGTCTGTGT | TCCTGTCCAT | CACTGATGCT | GCTGGCTACT | GCATGTGCCA | CACCTGTCTG | 2460 |
| TTCGCCATTC | CTAACATTCT | GTTTCATTCT | TCCTCGGGAG | ATATTTCAAA | CATTTGGTCT | 2520 |
| TTTCTTTTAA | CACTGAGGGT | AGGCCCTTAG | GAAATTTATT | TAGGAAAGTC | TGAACACGTT | 2580 |
| ATCACTTGGT | TTTCTGGAAA | GTAGCTTACC | CTAGAAAACA | GCTGCAAATG | CCAGAAAGAT | 2640 |
| GATCCCTAAA | AATGTTGAGG | GACTTCTGTT | CATTCATCCC | GAGAACATTG | GCTTCCACAT | 2700 |
| CACAGTATCT | ACCCTTACAT | GGTTTAGGAT | TAAAGCCAGG | CAATCTTTTA | CTATGAAAAA | 2760 |
| AAAAAAAAAA | AAAAAAAAAA | AAAA | | | | 2784 |

(2) INFORMATION FOR SEQ ID NO:2:

(i) SEQUENCE CHARACTERISTICS:
    (A) LENGTH: 557 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:2:

Met Met Val Val Leu Leu Gly Ala Thr Thr Leu Val Leu Val Ala Val
1               5                   10                  15

Gly Pro Trp Val Leu Ser Ala Ala Ala Gly Gly Lys Asn Leu Lys Ser
            20                  25                  30

```
Pro Gln Lys Val Glu Val Asp Ile Ile Asp Asp Asn Phe Ile Leu Arg
         35                  40                 45

Trp Asn Arg Ser Asp Glu Ser Val Gly Asn Val Thr Phe Ser Phe Asp
         50                  55              60

Tyr Gln Lys Thr Gly Met Asp Asn Trp Ile Lys Leu Ser Gly Cys Gln
65                       70              75                    80

Asn Ile Thr Ser Thr Lys Cys Asn Phe Ser Ser Leu Lys Leu Asn Val
                 85                  90                 95

Tyr Glu Glu Ile Lys Leu Arg Ile Arg Ala Glu Lys Glu Asn Thr Ser
            100                 105                110

Ser Trp Tyr Glu Val Asp Ser Phe Thr Pro Phe Arg Lys Ala Gln Ile
            115                 120             125

Gly Pro Pro Glu Val His Leu Glu Ala Glu Asp Lys Ala Ile Val Ile
        130                 135             140

His Ile Ser Pro Gly Thr Lys Asp Ser Val Met Trp Ala Leu Asp Gly
145                     150                 155                160

Leu Ser Phe Thr Tyr Ser Leu Leu Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190

Ser Pro Glu Thr Thr Tyr Cys Leu Lys Val Lys Ala Ala Leu Leu Thr
            195                 200             205

Ser Trp Lys Ile Gly Val Tyr Ser Pro Val His Cys Ile Lys Thr Thr
        210                 215             220

Val Glu Asn Glu Leu Pro Pro Glu Asn Ile Glu Val Ser Val Gln
225                 230             235                     240

Asn Gln Asn Tyr Val Leu Lys Trp Asp Tyr Thr Tyr Ala Asn Met Thr
                245                 250                 255

Phe Gln Val Gln Trp Leu His Ala Phe Leu Lys Arg Asn Pro Gly Asn
        260                 265             270

His Leu Tyr Lys Trp Lys Gln Ile Pro Asp Cys Glu Asn Val Lys Thr
        275                 280             285

Thr Gln Cys Val Phe Pro Gln Asn Val Phe Gln Lys Gly Ile Tyr Leu
    290                 295             300

Leu Arg Val Gln Ala Ser Asp Gly Asn Asn Thr Ser Phe Trp Ser Glu
305                 310             315                     320

Glu Ile Lys Phe Asp Thr Glu Ile Gln Ala Phe Leu Leu Pro Pro Val
            325                 330             335

Phe Asn Ile Arg Ser Leu Ser Asp Ser Phe His Ile Tyr Ile Gly Ala
            340                 345             350

Pro Lys Gln Ser Gly Asn Thr Pro Val Ile Gln Asp Tyr Pro Leu Ile
            355             360             365

Tyr Glu Ile Ile Phe Trp Glu Asn Thr Ser Asn Ala Glu Arg Lys Ile
    370                 375             380

Ile Glu Lys Lys Thr Asp Val Thr Val Pro Asn Leu Lys Pro Leu Thr
385             390             395                     400

Val Tyr Cys Val Lys Ala Arg Ala His Thr Met Asp Glu Lys Leu Asn
            405                 410                 415

Lys Ser Ser Val Phe Ser Asp Ala Val Cys Glu Lys Thr Lys Pro Gly
            420                 425             430

Asn Thr Ser Lys Ile Trp Leu Ile Val Gly Ile Cys Ile Ala Leu Phe
        435                 440             445

Ala Leu Pro Phe Val Ile Tyr Ala Ala Lys Val Phe Leu Arg Cys Ile
450                 455             460
```

|     |     |     |     |     |     |     |     |     |     |     |     |     |     |     |     |
|-----|-----|-----|-----|-----|-----|-----|-----|-----|-----|-----|-----|-----|-----|-----|-----|
| Asn 465 | Tyr | Val | Phe | Phe | Pro 470 | Ser | Leu | Lys | Pro 475 | Ser | Ser | Ile | Asp | Glu 480 |
| Tyr | Phe | Ser | Glu | Gln 485 | Pro | Leu | Lys | Asn | Leu 490 | Leu | Leu | Ser | Thr | Ser 495 | Glu |
| Glu | Gln | Ile | Glu 500 | Lys | Cys | Phe | Ile | Ile 505 | Glu | Asn | Ile | Ser | Thr 510 | Ile | Ala |
| Thr | Val | Glu 515 | Glu | Thr | Asn | Gln | Thr 520 | Asp | Glu | Asp | His | Lys 525 | Lys | Tyr | Ser |
| Ser | Gln 530 | Thr | Ser | Gln | Asp | Ser 535 | Gly | Asn | Tyr | Ser | Asn 540 | Glu | Asp | Glu | Ser |
| Glu 545 | Ser | Lys | Thr | Ser | Glu 550 | Glu | Leu | Gln | Gln | Asp 555 | Phe | Val |